(12) United States Patent
Altenbuchner et al.

(10) Patent No.: US 6,713,288 B1
(45) Date of Patent: Mar. 30, 2004

(54) WHOLE CELL CATALYSTS

(75) Inventors: Josef Altenbuchner, Nufringen (DE); Andreas Bommarius, Frankfurt (DE); Ralf Mattes, Stuttgart (DE); Christoph Syldatk, Stuttgart (DE); Wilhelm Tischer, Peissenberg (DE); Anja Wiese, Eching (DE); Burkard Wilms, Stuttgart (DE)

(73) Assignees: University of Stuttgart, Stuttgart (DE); Degussa AG, Hanau-Wolfgang (DE)

( * ) Notice: Subject to any disclaimer, the term of this patent is extended or adjusted under 35 U.S.C. 154(b) by 0 days.

(21) Appl. No.: 09/407,062

(22) Filed: Sep. 28, 1999

(51) Int. Cl.$^7$ .................. C12P 13/04; C12N 15/70; C12N 1/20; C12N 5/10; C12N 9/00

(52) U.S. Cl. .................. 435/106; 435/183; 435/320.1; 435/325; 435/252.3; 435/471; 435/252.33; 435/476; 435/488; 435/489

(58) Field of Search .............. 435/183, 320.1, 435/325, 252.3, 106, 471, 252.33, 476, 488, 489

(56) References Cited

U.S. PATENT DOCUMENTS 5,516,660 A * 5/1996 Wagner et al. .............. 435/106

FOREIGN PATENT DOCUMENTS

JP 03251176 8/1991

OTHER PUBLICATIONS

Bork, Genome Research, 10:398–400, 2000.*
Broun et al., Science 282:1315–1317, 1998.*
Van de Loo et al., Proc. Natl. Acad. Sci. 92:6743–6747, 1995.*
K. Watabe et al., *Identification and Sequencing of a Gene Encoding a Hydantoin Racemase from the Native Plasmid of Pseudomonas–SP Strain NS671*, Journal of Bacteriology, vol. 174, No. 11, 1992, pp. 3461–3466.

R. Grifantini et al., *Efficient Conversion of 5–Substituted Hydantoins to D–α–amino Acids Using Recombinant Escherichia coli Strains*, Microbiology, vol. 144, 947–954, 1998.
M. Siemann et al., *Characterization of Serological Properties of Polyclonal Antibodies Produced Against Enzymes Involved in the L–Selective Cleavage of Hydanton Derivatives*, Bioctechnology Letters, vol. 15, No. 1 (Jan. 1993, pp. 1–6.
B. Wilms, et al., *Cloning, Nucleotide Sequence and Expression of a New L–N–Carbamoylase Gene From Arthrobacter Aurescens DSM 3747 in E. Coli*, Journal of Biotechnology, vol. 68, pp. 101–113, 1999.
F. Blattner, et al., *The Complete Genome Sequence of Escherichia coli K–12*, Science, vol. 277, No. 5331, pp. 1453–1462, 1997.
J. Lebowitz, *Plasmid ColE1, Complete Geonome*, Database Genbank, Acc No. J01566, Feb. 8, 1996, XP002154850.
O. May, et al., *Inverting Enantioselectivity by Directed Evolution of Hydantoinase for Improved Production of L–Methionine*, Nature Biotechnology, vol. 18, No. 3, Mar. 2000; pp. 317–320.
A. Wiese et al., *Hydantoin Racemase from Arthrobacter Aurescens, DSM 3747: Heterologous Expression, Purification and Characterization*, Journal of Biotechnology, vol. 80, pp. 217–230, 2000.
K. Watabe et al., *Cloning and Sequencing of the Genes Involved in the Conversion of 5–Substituted Hydantoins to the Corresponding L–Amino Acids from the Native Plasmid of Pseudomonas sp. Strain NS671*, Journal of Bacteriology, vol. 174, No. 3, Feb. 1992, pp. 962–969.

* cited by examiner

*Primary Examiner*—Rebecca E. Prouty
*Assistant Examiner*—Delia Ramirez
(74) *Attorney, Agent, or Firm*—Oblon, Spivak, McClelland, Maier & Neustadt, P.C.

(57) ABSTRACT

A microorganism is described which is transformed with DNAs which encode a hydantoinnase, a racemase, and a carbamoylase. As a result, the microorganism is able to degrade hydantoins directly to amino acids. A process for the production of the microorganism and a process for producing amino acids with the microorganism is also described.

56 Claims, 10 Drawing Sheets

SEQUENCE LISTING

```
<160> NUMBER OF SEQ ID NOS: 11

<210> SEQ ID NO 1
<211> LENGTH: 30
<212> TYPE: DNA
<213> ORGANISM: Artificial Sequence
<220> FEATURE:
<223> OTHER INFORMATION: Synthetic DNA

<400> SEQUENCE: 1
aaaaaagctt ttaagaagga gatatacata                                    30

<210> SEQ ID NO 2
<211> LENGTH: 27
<212> TYPE: DNA
<213> ORGANISM: Artificial Sequence
<220> FEATURE:
<223> OTHER INFORMATION: Synthetic DNA

<400> SEQUENCE: 2
aaagcatgca tggcccttcg ctgggat                                       27

<210> SEQ ID NO 3
<211> LENGTH: 24
<212> TYPE: DNA
<213> ORGANISM: Artificial Sequence
<220> FEATURE:
```

-continued

<223> OTHER INFORMATION: Synthetic DNA

<400> SEQUENCE: 3
aaagcatgca tggctacgag ggca                                              24

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
aaacaagatc tcgcgactgg                                                   20

<210> SEQ ID NO 5
<211> LENGTH: 31
<212> TYPE: DNA
<213> ORGANISM: Artificial Sequence
<220> FEATURE:
<223> OTHER INFORMATION: Synthetic DNA

<400> SEQUENCE: 5
aaaaagatct ttatcaggcc tacaactgtt g                                      31

<210> SEQ ID NO 6
<211> LENGTH: 1239
<212> TYPE: DNA
<213> ORGANISM: Arthrobacter aurescens
<220> FEATURE:
<221> NAME/KEY: CDS
<222> LOCATION: (1)..(1239)
<223> OTHER INFORMATION:

<400> SEQUENCE: 6

```
atg acc ctg cag aaa gcg caa gcg gcg cgc att gag aaa gag atc cgg        48
Met Thr Leu Gln Lys Ala Gln Ala Ala Arg Ile Glu Lys Glu Ile Arg
1               5                   10                  15 gag ctc tcc cgg ttc tcg gca gaa ggc ccc ggt gtt acc cgg ctg acc        96
Glu Leu Ser Arg Phe Ser Ala Glu Gly Pro Gly Val Thr Arg Leu Thr
                20                  25                  30 tac act cca gag cat gcc gcc gcg cgg gaa acg ctc att gcg gct atg       144
Tyr Thr Pro Glu His Ala Ala Ala Arg Glu Thr Leu Ile Ala Ala Met
            35                  40                  45 aaa gcg gcc gcc ttg agc gtt cgt gaa gac gca ctc gga aac atc atc       192
Lys Ala Ala Ala Leu Ser Val Arg Glu Asp Ala Leu Gly Asn Ile Ile
        50                  55                  60 ggc cga cgt gaa ggc act gat ccg gag ctt cct gcg atc gcg tcg ggt       240
Gly Arg Arg Glu Gly Thr Asp Pro Glu Leu Pro Ala Ile Ala Val Gly
65                  70                  75                  80 tca cac ttc gat tct gtc cga aac ggc ggg atg ttt gat ggc act gca       288
Ser His Phe Asp Ser Val Arg Asn Gly Gly Met Phe Asp Gly Thr Ala
                85                  90                  95 ggc gtg gtg tgc gcc ctt gag gct gcc cgg gtg atg ctg gag aac ggc       336
Gly Val Val Cys Ala Leu Glu Ala Ala Arg Val Met Leu Glu Asn Gly
            100                 105                 110 tac gtg aat cgg cat cca ttt gag ttc atc gcg atc gtg gag gag gaa       384
Tyr Val Asn Arg His Pro Phe Glu Phe Ile Ala Ile Val Glu Glu Glu
        115                 120                 125 ggg gcc cgc ttc agc agt ggc atg ttg ggc ggc cgg gcc att gca ggg       432
Gly Ala Arg Phe Ser Ser Gly Met Leu Gly Gly Arg Ala Ile Ala Gly
    130                 135                 140 ttg gtc gcc gac agg gaa ctg gac tct ttg gtt gat gag gat gga gtg       480
```

```
Leu Val Ala Asp Arg Glu Leu Asp Ser Leu Val Asp Glu Asp Gly Val
145                 150                 155                 160 tcc gtt agg cag gcg gct act gcc ttc ggc ttg aag ccg ggc gaa ctg    528
Ser Val Arg Gln Ala Ala Thr Ala Phe Gly Leu Lys Pro Gly Glu Leu
                165                 170                 175 cag gct gca gcc cgc tcc gcg gcg gac ctg cgt gct ttt atc gaa cta    576
Gln Ala Ala Ala Arg Ser Ala Ala Asp Leu Arg Ala Phe Ile Glu Leu
            180                 185                 190 cac att gaa caa gga ccg atc ctc gag cag gag caa ata gag atc gga    624
His Ile Glu Gln Gly Pro Ile Leu Glu Gln Glu Gln Ile Glu Ile Gly
        195                 200                 205 gtt gta acc tcc atc gtt ggc gtt cgc gca ttg cgg gtt gcc gtc aaa    672
Val Val Thr Ser Ile Val Gly Val Arg Ala Leu Arg Val Ala Val Lys
    210                 215                 220 ggc aga agc gac cac gcc ggc aca acc ccc atg cac ctg cgc cag gat    720
Gly Arg Ser Asp His Ala Gly Thr Thr Pro Met His Leu Arg Gln Asp
225                 230                 235                 240 gcg ctg gta ccc gcc gct ctc atg gtg agg gag gtc aac cgg ttc gtc    768
Ala Leu Val Pro Ala Ala Leu Met Val Arg Glu Val Asn Arg Phe Val
                245                 250                 255 aac gag atc gcc gat ggc aca gtg gct acc gtt ggc cac ctc aca gtg    816
Asn Glu Ile Ala Asp Gly Thr Val Ala Thr Val Gly His Leu Thr Val
            260                 265                 270 gcc ccc ggt gga ggc aac cag gtc ccg ggg gag gtg gac ttc aca ctg    864
Ala Pro Gly Gly Gly Asn Gln Val Pro Gly Glu Val Asp Phe Thr Leu
        275                 280                 285 gac ctg cgt tct ccg cat gag gag tcg ctc cgc gtg ctg atc gac cgc    912
Asp Leu Arg Ser Pro His Glu Glu Ser Leu Arg Val Leu Ile Asp Arg
    290                 295                 300 atc tcg gtc atg gtc ggc gag gtc gcc tcc cag gcc ggt gtg gct gcc    960
Ile Ser Val Met Val Gly Glu Val Ala Ser Gln Ala Gly Val Ala Ala
305                 310                 315                 320 gat gtg gat gaa ttt ttc aat ctc agc ccg gtg cag ctg gct cct acc    1008
Asp Val Asp Glu Phe Phe Asn Leu Ser Pro Val Gln Leu Ala Pro Thr
                325                 330                 335 atg gtg gac gcc gtt cgc gaa gcg gcc tcg gcc ttg cag ttc aca cac    1056
Met Val Asp Ala Val Arg Glu Ala Ala Ser Ala Leu Gln Phe Thr His
            340                 345                 350 cgg gat atc agc agt ggg gcg ggc cac gac tcg atg ttc atc gcc cag    1104
Arg Asp Ile Ser Ser Gly Ala Gly His Asp Ser Met Phe Ile Ala Gln
        355                 360                 365 gtc acg gac gtc gga atg gtt ttc gtt cca agc cgt gct ggc cgg agc    1152
Val Thr Asp Val Gly Met Val Phe Val Pro Ser Arg Ala Gly Arg Ser
    370                 375                 380 cac gtt ccc gaa gaa tgg acc gat ttc gat gac ctt cgc aaa gga act    1200
His Val Pro Glu Glu Trp Thr Asp Phe Asp Asp Leu Arg Lys Gly Thr
385                 390                 395                 400 gag gtt gtc ctc cgg gta atg aag gca ctt gac cgg taa                1239
Glu Val Val Leu Arg Val Met Lys Ala Leu Asp Arg
                405                 410

<210> SEQ ID NO 7
<211> LENGTH: 412
<212> TYPE: PRT
<213> ORGANISM: Arthrobacter aurescens

<400> SEQUENCE: 7

Met Thr Leu Gln Lys Ala Gln Ala Ala Arg Ile Glu Lys Glu Ile Arg
1               5                   10                  15

Glu Leu Ser Arg Phe Ser Ala Glu Gly Pro Gly Val Thr Arg Leu Thr
```

```
                    20                  25                  30
Tyr Thr Pro Glu His Ala Ala Arg Glu Thr Leu Ile Ala Ala Met
        35                  40                  45
Lys Ala Ala Leu Ser Val Arg Glu Asp Ala Leu Gly Asn Ile Ile
 50                  55                  60
Gly Arg Glu Gly Thr Asp Pro Glu Leu Pro Ala Ile Ala Val Gly
 65                  70                  75                  80
Ser His Phe Asp Ser Val Arg Asn Gly Met Phe Asp Gly Thr Ala
             85                  90                  95
Gly Val Val Cys Ala Leu Glu Ala Ala Arg Val Met Leu Glu Asn Gly
                100                 105                 110
Tyr Val Asn Arg His Pro Phe Glu Phe Ile Ala Ile Val Glu Glu Glu
                115                 120                 125
Gly Ala Arg Phe Ser Ser Gly Met Leu Gly Gly Arg Ala Ile Ala Gly
 130                 135                 140
Leu Val Ala Asp Arg Glu Leu Asp Ser Leu Val Asp Glu Asp Gly Val
 145                 150                 155                 160
Ser Val Arg Gln Ala Ala Thr Ala Phe Gly Leu Lys Pro Gly Glu Leu
                165                 170                 175
Gln Ala Ala Ala Arg Ser Ala Ala Asp Leu Arg Ala Phe Ile Glu Leu
                180                 185                 190
His Ile Glu Gln Gly Pro Ile Leu Glu Gln Glu Gln Ile Glu Ile Gly
                195                 200                 205
Val Val Thr Ser Ile Val Gly Val Arg Ala Leu Arg Val Ala Val Lys
 210                 215                 220
Gly Arg Ser Asp His Ala Gly Thr Thr Pro Met His Leu Arg Gln Asp
 225                 230                 235                 240
Ala Leu Val Pro Ala Ala Leu Met Val Arg Glu Val Asn Arg Phe Val
                245                 250                 255
Asn Glu Ile Ala Asp Gly Thr Val Ala Thr Val Gly His Leu Thr Val
                260                 265                 270
Ala Pro Gly Gly Gly Asn Gln Val Pro Gly Glu Val Asp Phe Thr Leu
                275                 280                 285
Asp Leu Arg Ser Pro His Glu Glu Ser Leu Arg Val Leu Ile Asp Arg
 290                 295                 300
Ile Ser Val Met Val Gly Glu Val Ala Ser Gln Ala Gly Val Ala Ala
 305                 310                 315                 320
Asp Val Asp Glu Phe Phe Asn Leu Ser Pro Val Gln Leu Ala Pro Thr
                325                 330                 335
Met Val Asp Ala Val Arg Glu Ala Ala Ser Ala Leu Gln Phe Thr His
                340                 345                 350
Arg Asp Ile Ser Ser Gly Ala Gly His Asp Ser Met Phe Ile Ala Gln
                355                 360                 365
Val Thr Asp Val Gly Met Val Phe Val Pro Ser Arg Ala Gly Arg Ser
 370                 375                 380
His Val Pro Glu Glu Trp Thr Asp Phe Asp Asp Leu Arg Lys Gly Thr
 385                 390                 395                 400
Glu Val Val Leu Arg Val Met Lys Ala Leu Asp Arg
                405                 410

<210> SEQ ID NO 8
<211> LENGTH: 1377
<212> TYPE: DNA
<213> ORGANISM: Arthrobacter aurescens
```

-continued

```
<220> FEATURE:
<221> NAME/KEY: CDS
<222> LOCATION: (1)..(1377)
<223> OTHER INFORMATION:

<400> SEQUENCE: 8 atg ttt gac gta ata gtt aag aac tgc cgt atg gtg tcc agc gac gga        48
Met Phe Asp Val Ile Val Lys Asn Cys Arg Met Val Ser Ser Asp Gly
1               5                   10                  15 atc acc gag gca gac att ctg gtg aaa gac ggc aaa gtc gcc gca atc        96
Ile Thr Glu Ala Asp Ile Leu Val Lys Asp Gly Lys Val Ala Ala Ile
            20                  25                  30 agc gcg gac aca cgt gat gtc gag gcc agc cga acc att gac gcg ggt       144
Ser Ala Asp Thr Arg Asp Val Glu Ala Ser Arg Thr Ile Asp Ala Gly
        35                  40                  45 ggc aag ttc gtg atg ccg ggc gtg gtc gat gaa cat gtg cat atc atc       192
Gly Lys Phe Val Met Pro Gly Val Val Asp Glu His Val His Ile Ile
    50                  55                  60 gac atg gat ctc aag aac cgg tat ggc cgc ttc gaa ctc gat tcc gag       240
Asp Met Asp Leu Lys Asn Arg Tyr Gly Arg Phe Glu Leu Asp Ser Glu
65                  70                  75                  80 tct gcg gcc gtg gga ggc atc acc acc atc atc gag atg ccg atc acc       288
Ser Ala Ala Val Gly Gly Ile Thr Thr Ile Ile Glu Met Pro Ile Thr
                85                  90                  95 ttc cca ccc acc acc act ctg gac gcc ttc ctt gaa aag aag aag cag       336
Phe Pro Pro Thr Thr Thr Leu Asp Ala Phe Leu Glu Lys Lys Lys Gln
            100                 105                 110 gcg ggg cag cgg ttg aaa gtt gac ttc gcg ctc tat gga ggt gga gtg       384
Ala Gly Gln Arg Leu Lys Val Asp Phe Ala Leu Tyr Gly Gly Gly Val
        115                 120                 125 ccg gga aac ctg ccc gag atc cgc aaa atg cac gac gcc ggc gct gtg       432
Pro Gly Asn Leu Pro Glu Ile Arg Lys Met His Asp Ala Gly Ala Val
    130                 135                 140 ggc ttc aag tca atg atg gca gcc tca gtg ccg ggc atg ttc gac gcc       480
Gly Phe Lys Ser Met Met Ala Ala Ser Val Pro Gly Met Phe Asp Ala
145                 150                 155                 160 gtc agc gac ggc gaa ctg ttc gaa atc ttc caa gag atc gca gcc tgt       528
Val Ser Asp Gly Glu Leu Phe Glu Ile Phe Gln Glu Ile Ala Ala Cys
                165                 170                 175 ggt tca gtc atc gtg gtt cat gcc gag aat gaa acg atc att caa gcg       576
Gly Ser Val Ile Val Val His Ala Glu Asn Glu Thr Ile Ile Gln Ala
            180                 185                 190 ctc cag aag cag atc aag gcc gct ggc ggc aag gac atg gcc gcc tac       624
Leu Gln Lys Gln Ile Lys Ala Ala Gly Gly Lys Asp Met Ala Ala Tyr
        195                 200                 205 gag gca tcc caa cca gtt ttc cag gag aac gag gcc att cag cgt gcg       672
Glu Ala Ser Gln Pro Val Phe Gln Glu Asn Glu Ala Ile Gln Arg Ala
    210                 215                 220 ttg ctt ctg cag aaa gaa gcc ggc tgt cga ctg atc gtg ctt cac gtg       720
Leu Leu Leu Gln Lys Glu Ala Gly Cys Arg Leu Ile Val Leu His Val
225                 230                 235                 240 agc aac cct gac ggc gtc gag tta ata cat cag gcg caa tcc gag ggt       768
Ser Asn Pro Asp Gly Val Glu Leu Ile His Gln Ala Gln Ser Glu Gly
                245                 250                 255 cag gac gtc cac tgc gag tcg ggt ccg cag tat ctg aat atc acc acg       816
Gln Asp Val His Cys Glu Ser Gly Pro Gln Tyr Leu Asn Ile Thr Thr
            260                 265                 270 gac gac gcc gaa cga atc gga ccg tat atg aag gtc gcg ccg ccc gtc       864
Asp Asp Ala Glu Arg Ile Gly Pro Tyr Met Lys Val Ala Pro Pro Val
        275                 280                 285
```

```
cgc tca gcc gaa atg aac gtc agg tta tgg gaa caa ctc gag aac ggt    912
Arg Ser Ala Glu Met Asn Val Arg Leu Trp Glu Gln Leu Glu Asn Gly
    290                 295                 300 gtc atc gac acc ctt gga tca gat cat ggc gga cat cct gtc gag gac    960
Val Ile Asp Thr Leu Gly Ser Asp His Gly Gly His Pro Val Glu Asp
305                 310                 315                 320 aaa gaa ccc ggc tgg aag gac gtg tgg aaa gcc ggc aac ggt gcg ctg   1008
Lys Glu Pro Gly Trp Lys Asp Val Trp Lys Ala Gly Asn Gly Ala Leu
                325                 330                 335 ggc ctt gag aca tcc ctg cct atg atg ctg acc aac gga gtg aac aag   1056
Gly Leu Glu Thr Ser Leu Pro Met Met Leu Thr Asn Gly Val Asn Lys
        340                 345                 350 ggc agg cta tcc ttg gaa cgc ctc gtc gag gtg atg tgc gag aaa cct   1104
Gly Arg Leu Ser Leu Glu Arg Leu Val Glu Val Met Cys Glu Lys Pro
            355                 360                 365 gcg aag ctt ttt ggt atc tat ccg cag aag ggc acg cta cag gtt ggt   1152
Ala Lys Leu Phe Gly Ile Tyr Pro Gln Lys Gly Thr Leu Gln Val Gly
    370                 375                 380 tcc gac gcc gat cta ctc atc ctc gat ctg gac att gac acc aaa gtg   1200
Ser Asp Ala Asp Leu Leu Ile Leu Asp Leu Asp Ile Asp Thr Lys Val
385                 390                 395                 400 gat gcg tcg cag ttc cga tcc ctg cat aag tac agc ccg ttc gac ggg   1248
Asp Ala Ser Gln Phe Arg Ser Leu His Lys Tyr Ser Pro Phe Asp Gly
                405                 410                 415 atg ccc gtc acg ggt gca ccg gtt ctg acg atg gtg cgc gga acg gtg   1296
Met Pro Val Thr Gly Ala Pro Val Leu Thr Met Val Arg Gly Thr Val
        420                 425                 430 gtg gcc gag cag gga gaa gtt ctg gtc gag cag gga ttc ggc cag ttc   1344
Val Ala Glu Gln Gly Glu Val Leu Val Glu Gln Gly Phe Gly Gln Phe
            435                 440                 445 gtc acc cgt cac cac tac gag gcg tcg aag tga                        1377
Val Thr Arg His His Tyr Glu Ala Ser Lys
    450                 455

<210> SEQ ID NO 9
<211> LENGTH: 458
<212> TYPE: PRT
<213> ORGANISM: Arthrobacter aurescens

<400> SEQUENCE: 9

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ala Asp Thr Arg Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140
```

-continued

```
Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Ile Val His Ala Glu Asn Glu Thr Ile Ile Gln Ala
            180                 185                 190

Leu Gln Lys Gln Ile Lys Ala Ala Gly Gly Lys Asp Met Ala Ala Tyr
                195                 200                 205

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
    290                 295                 300

Val Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
    355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Gln Gly Glu Val Leu Val Glu Gln Gly Phe Gly Gln Phe
            435                 440                 445

Val Thr Arg His His Tyr Glu Ala Ser Lys
    450                 455
```

<210> SEQ ID NO 10
<211> LENGTH: 711
<212> TYPE: DNA
<213> ORGANISM: Arthrobacter aurescens
<220> FEATURE:
<221> NAME/KEY: CDS
<222> LOCATION: (1)..(711)
<223> OTHER INFORMATION:

<400> SEQUENCE: 10

```
atg aga atc ctc gtg atc aac ccc aac agt tcc agc gcc ctt act gaa    48
Met Arg Ile Leu Val Ile Asn Pro Asn Ser Ser Ser Ala Leu Thr Glu
1               5                   10                  15 tcg gtt gcg gac gca gca caa caa gtt gtc gcg acc ggc acc ata att    96
Ser Val Ala Asp Ala Ala Gln Gln Val Val Ala Thr Gly Thr Ile Ile
                20                  25                  30
```

```
tct gcc atc aac ccc tcc aga gga ccc gcc gtc att gaa ggc agc ttt      144
Ser Ala Ile Asn Pro Ser Arg Gly Pro Ala Val Ile Glu Gly Ser Phe
         35                  40                  45 gac gaa gca ctg gcc acg ttc cat ctc att gaa gag gtg gag cgc gct      192
Asp Glu Ala Leu Ala Thr Phe His Leu Ile Glu Glu Val Glu Arg Ala
     50                  55                  60 gag cgg gaa aac ccg ccc gac gcc tac gtc atc gca tgt ttc ggg gat      240
Glu Arg Glu Asn Pro Pro Asp Ala Tyr Val Ile Ala Cys Phe Gly Asp
 65                  70                  75                  80 ccg gga ctt gac gcg gtc aag gag ctg act gac agg cca gtg gta gga      288
Pro Gly Leu Asp Ala Val Lys Glu Leu Thr Asp Arg Pro Val Val Gly
                 85                  90                  95 gtt gcc gaa gct gca atc cac atg tct tca ttc gtc gcg gcc acc ttc      336
Val Ala Glu Ala Ala Ile His Met Ser Ser Phe Val Ala Ala Thr Phe
            100                 105                 110 tcc att gtc agc atc ctc ccg agg gtc agg aaa cat ctg cac gaa ctg      384
Ser Ile Val Ser Ile Leu Pro Arg Val Arg Lys His Leu His Glu Leu
        115                 120                 125 gta cgg caa gcg ggg gcg acg aat cgc ctc gcc tcc atc aag ctc cca      432
Val Arg Gln Ala Gly Ala Thr Asn Arg Leu Ala Ser Ile Lys Leu Pro
    130                 135                 140 aat ctg ggg gtg atg gcc ttc cat gag gac gaa cat gcc gca ctg gag      480
Asn Leu Gly Val Met Ala Phe His Glu Asp Glu His Ala Ala Leu Glu
145                 150                 155                 160 acg ctc aaa caa gcc gcc aag gag gcg gtc cag gag gac ggc gcc gag      528
Thr Leu Lys Gln Ala Ala Lys Glu Ala Val Gln Glu Asp Gly Ala Glu
                165                 170                 175 tcg ata gtg ctc gga tgc gcc ggc atg gtg ggg ttt gcg cgt caa ctg      576
Ser Ile Val Leu Gly Cys Ala Gly Met Val Gly Phe Ala Arg Gln Leu
            180                 185                 190 agc gac gaa ctc ggc gtc cct gtc atc gac ccc gtc gag gca gct tgc      624
Ser Asp Glu Leu Gly Val Pro Val Ile Asp Pro Val Glu Ala Ala Cys
        195                 200                 205 cgc gtg gcc gag agt ttg gtc gct ctg ggc tac cag acc agc aaa gcg      672
Arg Val Ala Glu Ser Leu Val Ala Leu Gly Tyr Gln Thr Ser Lys Ala
    210                 215                 220 aac tcg tat caa aaa ccg aca gag aag cag tac ctc tag                  711
Asn Ser Tyr Gln Lys Pro Thr Glu Lys Gln Tyr Leu
225                 230                 235
```

<210> SEQ ID NO 11
<211> LENGTH: 236
<212> TYPE: PRT
<213> ORGANISM: Arthrobacter aurescens

<400> SEQUENCE: 11

```
Met Arg Ile Leu Val Ile Asn Pro Asn Ser Ser Ala Leu Thr Glu
 1               5                  10                  15

Ser Val Ala Asp Ala Ala Gln Gln Val Val Ala Thr Gly Thr Ile Ile
                 20                  25                  30

Ser Ala Ile Asn Pro Ser Arg Gly Pro Ala Val Ile Glu Gly Ser Phe
         35                  40                  45

Asp Glu Ala Leu Ala Thr Phe His Leu Ile Glu Glu Val Glu Arg Ala
     50                  55                  60

Glu Arg Glu Asn Pro Pro Asp Ala Tyr Val Ile Ala Cys Phe Gly Asp
 65                  70                  75                  80

Pro Gly Leu Asp Ala Val Lys Glu Leu Thr Asp Arg Pro Val Val Gly
                 85                  90                  95
```

-continued

```
Val Ala Glu Ala Ala Ile His Met Ser Ser Phe Val Ala Ala Thr Phe
            100                 105                 110

Ser Ile Val Ser Ile Leu Pro Arg Val Arg Lys His Leu His Glu Leu
            115                 120             125

Val Arg Gln Ala Gly Ala Thr Asn Arg Leu Ala Ser Ile Lys Leu Pro
    130                 135             140

Asn Leu Gly Val Met Ala Phe His Glu Asp Glu His Ala Ala Leu Glu
145                 150                 155                 160

Thr Leu Lys Gln Ala Ala Lys Glu Ala Val Gln Glu Asp Gly Ala Glu
                165             170                 175

Ser Ile Val Leu Gly Cys Ala Gly Met Val Gly Phe Ala Arg Gln Leu
            180                 185                 190

Ser Asp Glu Leu Gly Val Pro Val Ile Asp Pro Val Glu Ala Ala Cys
            195                 200                 205

Arg Val Ala Glu Ser Leu Val Ala Leu Gly Tyr Gln Thr Ser Lys Ala
    210                 215             220

Asn Ser Tyr Gln Lys Pro Thr Glu Lys Gln Tyr Leu
225                 230             235
```

WHOLE CELL CATALYSTS

The present invention is directed to a micro-organism, which is able to degrade hydantoins to enantiomerically enriched amino acids. Especially, this micro-organism is equipped with cloned genes coding for the necessary enzymes.

Racemic 5-monosubstituted hydantoins can be chemically synthesized according to Bucherer-Berg method using aldehydes, ammonium bicarbonate and sodium cyanide as reactants. They are important precursors for the enzymatic production of D- and L-amino acids. With the increasing demand for optically pure amino acids a lot of effort has been made towards the isolation of microorganisms capable for stereospecific hydrolysis of the hydantoins and characterization of the enzymes (Syldatk and Pietzsch, "Hydrolysis and formation of hydantoins" (1995), VCH Verlag, Weinhein, pp. 403–434; Ogawa et al., J. Mol. Catal. B: Enzym 2 (1997), 163–176; Syldatk et al., Appl. Microbiol. Biotechnol. 51 (1999), 293–309). The asymmetric bioconversion to either L- or D-amino acids consists of three steps:

(i) chemical and/or enzymatic racemization of 5-substituted hydantoins
(ii) ring opening hydrolysis achieved by a hydantoinase and
(iii) hydrolysis of the N-carbamoyl amino acid produced by hydantoinase to the amino acid by carbamoylase.

Arthrobacter aurescens DSM 3747 is one of the few isolated microorganisms capable of converting 5-monosubstituted hydantoins to L-amino acids. The disadvantage of using A. aurescens cells as biocatalyst is the low enzyme activity. Especially the L-N-carbamoylase is the bottleneck for most substrates leading to an increase of the intermediate L-N-carbamoyl amino acid in the cell, which is not further converted to the corresponding amino acid. By combining the purified enzymes bottlenecks could be avoided but due to the low amounts of enzymes in the cells and loss of activity during the many necessary purification steps this process is not cost-effective.

All three genes encoding for the racemase hyuA (SEQ ID NO: 11), the L-specific hydantoinase hyuH (SEQ ID NO: 9) and the stereoselective L-N-carbamoylase (SEQ ID NO: 7) have been cloned in E. coli separately and expressed to high levels (about 10% of the total cell protein) (DE 19913741; J. Biotechnol., to be published). For in vitro catalysis the enzymes from the three recombinant strains can be produced and purified more cost-effective then from the Arthrobacter aurescens strain. Regarding the different enzyme activities towards the various substrates the enzymes can be combined in enzyme reactors at ratios optimized for each reaction.

It is an object of this invention to provide a further possibility of how a racemase, a hydantoinase and a D- or L-specific carbamoylase can act together in a process for the production of enantiomerically enriched amino acids from 5-monosubstituted hydantoins. Especially, this possibility should be suitable to be implemented in processes on technical scale, that is to say it has to be most cost-effective.

This is done by using a whole cell catalyst according to claim 1. Further preferred catalysts are subjects to claims depending from claim 1. Claims 6 to 9 are directed to a process for the production of the whole cell catalyst of the invention. Claims 10 and 11 protect a process for the production of enantiomerically enriched amino acids using the catalyst according to the invention.

Using whole cell catalysts comprising cloned genes encoding for a hydantoinase, for a hydantoin racemase and a D- or L-specific carbamoylase for the conversion of 5-monosubstituted hydantoins to L- or D-amino acids results in a fast and complete conversion of racemic mixtures of hydantoins to the corresponding L- or D-amino acids on industrial scale. This significantly reduces the production costs due to a reduction of fermentation and purification costs because all enzymes are produced in one strain.

Advantageously, a bacteria is used as cell, because of high reproduction rates and easy growing conditions to be applied. There are several bacteria known to the skilled worker which can be utilized in this respect. Preferably a Escheria coli can be used as cell and expression system in this regard (Yanisch-Perron et al. Gene (1985), 33, 103–109).

It is another positive embodiment of this invention that in principle all genes encoding for the hydantoinase, racemase and carbamoylase known to the artisan can be taken to be expressed in the whole cell catalyst. Preferably all genes can be taken from DSM 3747 (SEQ ID NO: 7, 9, 11).

The enzymes to be incorporated in the genetic code of the whole cell catalyst naturally possess different turnover rates. It is a drawback if the rates of co-working enzymes are not in line and intermediates accumulate during the production inside the cell. The overexpression of the hydantoinase gene in E. coli leads to the formation of inclusion bodies (Wiese et al., in preparation), which is unfavourable for a well balanced coexpression of all the three enzymes. Therefore, various attempts to "fine tune" the expression of these genes have been made. This can be done advantageously by overexpressing the hydantoinase genes in question according to their turnover rates. According to the DSM 3747-System the hydantoinase gene is overexpresses from plasmids with reduced copy numbers.

A further embodiment of the instant invention is directed to a process for the production of the whole cell catalyst according to the invention. In principle all plasmids known to the skilled worker can serve to carry the gene into the expression system. Preferably, plasmids derived from pSC101, pACYC184 or pBR322 are used to produce the catalyst. Most preferably plasmids pBW31 and pBW32, pBW34 and pBW35, pBW34 and pBW53, pBW32 or pBW34 are used in this respect. For the skilled worker plasmids and methods to produce plasmids can be deduced from Studier et al., Methods Enzymol. 1990, 185, 61–69 or brochures of Novagen, Promega, New England Biolabs, Clontech or Gibco BRL. More applicable plasmids, vectors can be found in: DNA cloning: a practical approach. Volume I–III, edited by D. M. Glover, IRL Press Ltd., Oxford, Washington D.C., 1985, 1987; Denhardt, D. T. and Colasanti, J.: A surey of vectors for regulating expression of cloned DNA in E. coli. In: Rodriguez, R. L. and Denhardt, D. T (eds), Vectors, Butterworth, Stoneham, Mass., 1987, pp179–204; Gene expression technology. In: Goeddel, D. V. (eds), Methods in Enzymology, Volume 185, Academic Press, Inc., San Diego, 1990; Sambrook, J., Fritsch, E. F. and Maniatis, T. 1989. Molecular cloning: a laboratory manual, $2^{nd}$ ed. Cold Spring Harbor Laboratory Press, Cold Spring Harbor, N.Y. They are incorporated by reference herewith.

Over-expression can be accomplished be means known to the skilled artisan, e.g. using constitutive or inducible expression systems as reviewed by Makrides (Makrides, 1996, Microbiol. Rev. 60, no. 3, 512–538)

Preferably, for expression of the enzymes a rhamnose inducible E. coli promoter cassette is used.

In addition, primers useful for the amplification of the gene of the invention in a PCR are protected similarly. Primers which are feasible are for example, primers S988

(SEQ ID NO: 6), S2480 (SEQ ID NO: 1), S2248 (SEQ ID NO: 2), S2249 (SEQ ID NO: 3), S2517 (SEQ ID NO: 4) or S2518 (SEQ ID NO: 5). Furthermore, all other primers which could serve to carry out this invention and which are known to the artisan are deemed to be useful in this sense. The finding of a suitable primer is done by comparison of known DNA-sequences or translation of amino acid sequences into the codon of the organism in question (e.g. for Streptomyces: Wright et al., Gene 1992, 113, 55–65). Similarities in amino acid sequences of proteins of so called superfamilies are useful in this regard, too (Firestine et al., Chemistry & Biology 1996, 3, 779–783). Additional information can be found in Oligonucleotide synthesis: a practical approach, edited by M. J. Gait, IRL Press Ltd, Oxford Washington D.C., 1984; PCR Protocols: A guide to methods and applications, edited by M. A. Innis, D. H. Gelfound, J. J. Sninsky and T. J. White. Academic Press, Inc., San Diego, 1990. Those strategies are incorporated by reference herewith.

Another aspect of the invention is a process for the production of enantiomerically enriched amino acids, which utilizes a whole cell catalyst according to the invention. Furthermore, a process is preferred that is performed in an enzyme-membrane-reactor (DE 19910691.6).

To adopt the turnover rate of all enzymes expressed in the whole cell catalyst to each other there are different methods to achieve this.

a) The genes are expressed with different promoters. The gene with the lowest activity is combined with the strongest promoter and vice versa. A disadvantage would be that for each gene a different inductor is necessary to induce the expression of all genes.

b) The genes are expressed with one promoter on a polycistronic messenger. The ratios of synthesis of the enzymes is influenced by changing or by mutation of the translation initiation region of each gene (the ribosomal binding site) which determines the efficiency of protein synthesis. This principle is realized in operons of microorganisms. The disadvantage is that the efficiency of a translation initiation region can not be predicted which means that for each gene many changes in the translation initiation region have to be made and tested (Grifantini et al., 1998, Microbiology, 144, 947–954).

c) The enzyme activity of each enzyme can be changed by mutation using error prone PCR (Fromant et al., 1995, Anal. Biochem. 224, 347–353) and DNA shuffling (Stemmer, 1994, Nature 370, 389–391). Again, this is very time consuming and costly.

d) Instead of mutagenizing genes to optimize their function in a reaction cascade, genes from different origins which encode enzymes with appropriate properties could be combined to an operon. This needs a large database describing such enzymes.

e) All genes are expressed from the same promoter but from replicons with different copy numbers. This can be the chromosome (single copy) or plasmids with low, moderate and high copy numbers. By constructing various compatible plasmids with different copy numbers and antibiotic markers carrying each the same cassette with the promoter and a polylinker sequence, genes of interest can be integrated into the plasmids in one step and the plasmids combined within one strain. This method allows a fast construction and testing of many combinations and with just one inducer in one fermentation all genes are expressed at different levels according to the plasmid copy number.

The following paragraphs show the transformation of Hydantoins to enantiomerically enriched amino acids.

Figure 1:
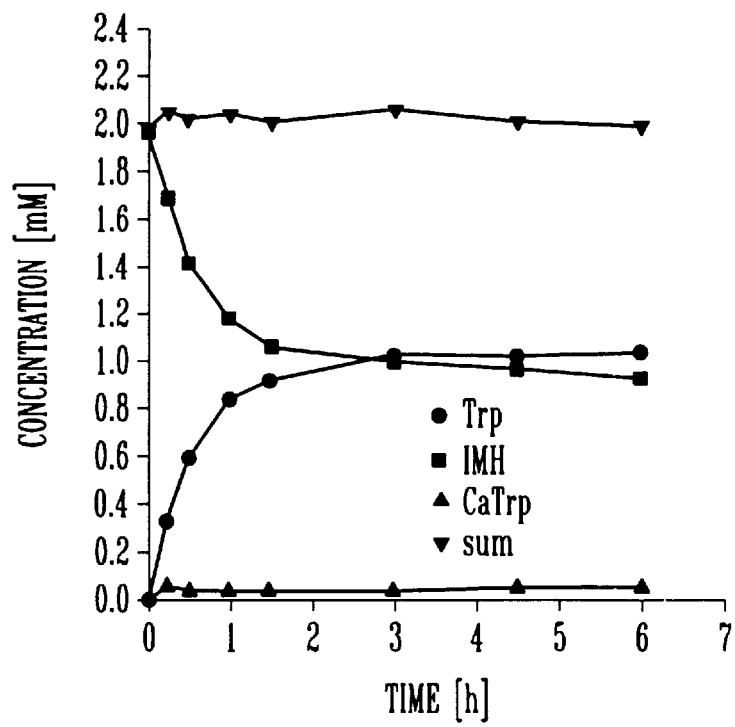
FIG. 1 shows the time course of conversions with *E. coli* BW3110 containing pAW229 and pBW31.
Figure 2:
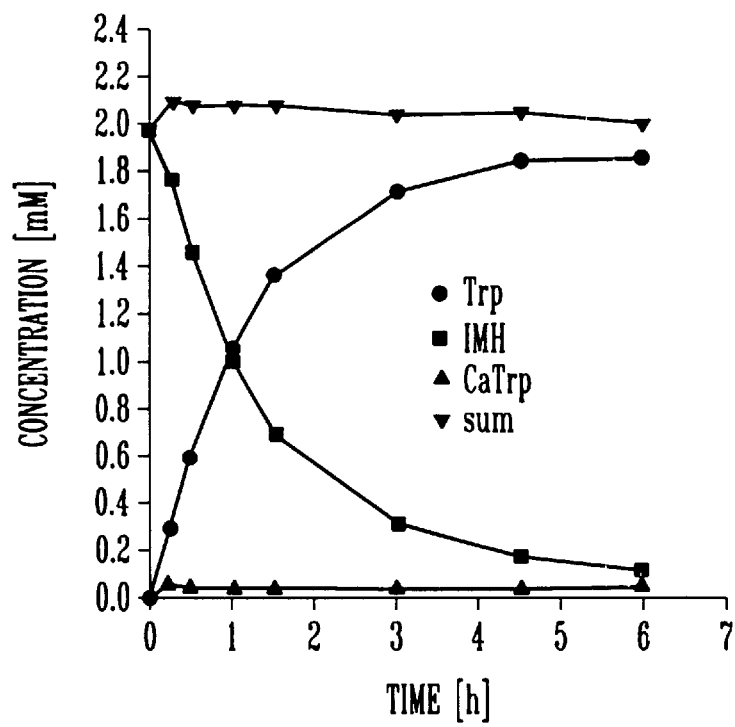
FIG. 2 shows the time course of conversions using pBW31 and pBW32.

Expression of the hyuA gene (SEQ ID NO: 11) is necessary for complete substrate conversion. FIG. 1 shows the time course of conversions with *E.coli* BW3110 containing pAW229 and pBW31. pAW 229 contains the carbamoylase gene on a pACYC plasmid, pBW31 is a pBR derivative and carries the hydantoinase gene. After consumption of 50% of the substrate, the reaction almost stops completely, since spontanous racemisation of IMH is very slow (Syldatk et. al., "Biocatalytic production of amino acids and derivatives" (1992), Hanser publishers, New York, pp. 75–176). As can be seen from FIG. 2, bringing the racemase (SEQ ID NO: 11) into the system by using pBW31 and pBW32, the pACYC plasmid with the carbamoylase and the racemase gene, enables complete conversion of the substrate. After 4.5 hours induction at 30° C. 200 μl permeabized cells were prepared as described above and were incubated with 800 μl of 2 mM D,L-IMH.

Figure 3:
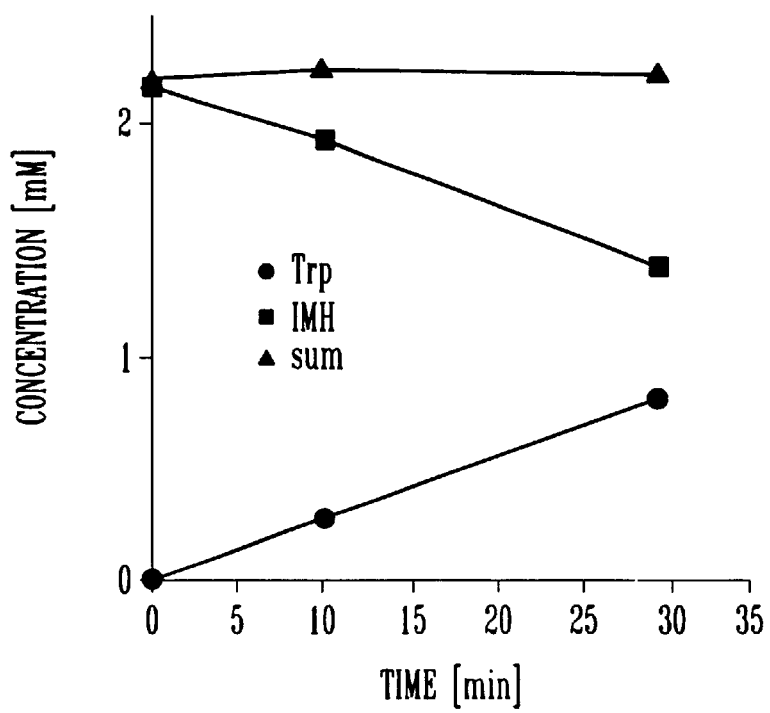
FIG. 3 shows the time course of conversions with *E. coli* BW3110H with the chromosomally integrated hydantoinase gene transformed with pBW32.
Figure 4:
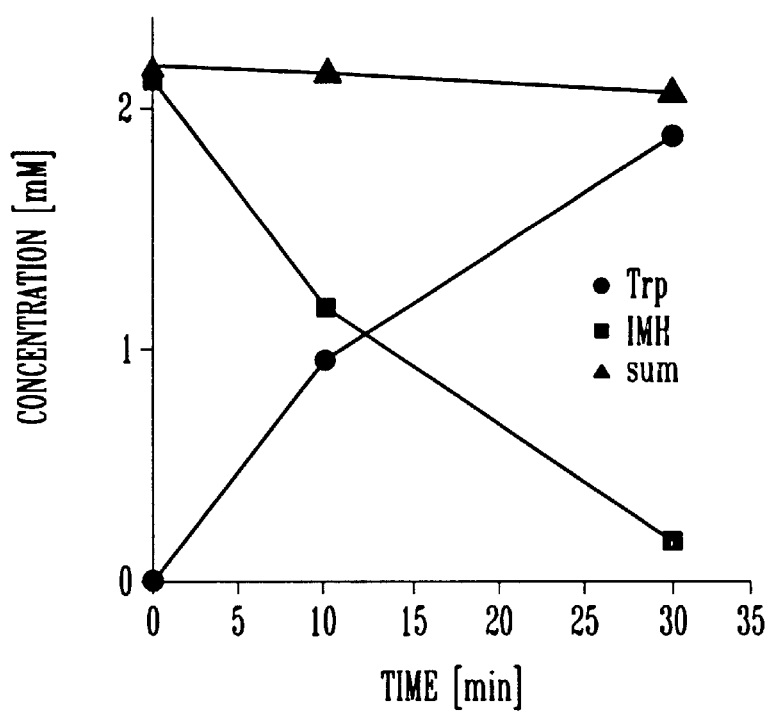
FIG. 4 shows the time course of conversions with *E. coli* BW3110H with the chromosomally integrated hydantoinase transformed with pBW34.

The *E. coli* strain BW3110H with the chromosomally integrated hydantoinase gene was transformed with pBW32 (FIG. 3), the pACYC plasmid containing the carbamoylase and the racemase gene, or with pBW34 (FIG. 4), the pBR plasmid containing the carbamoylase and the racemase gene. Cells were induced at 25° C. for 8.5 hours (pBW32), or for 11.5 hours (pBW34). Cell harvesting and permeabilization took place as described above.

Figure 5:
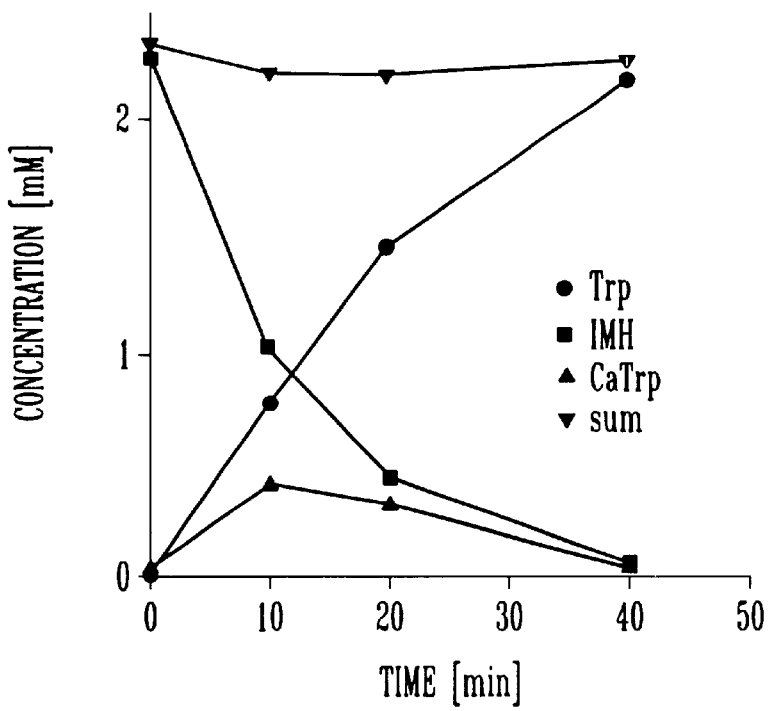
FIG. 5 shows the time course of conversions with *E. coli* BW3110 cells with pBW31 and pBW32. Cells were induced 10 hours at 30° C.

FIG. 5 shows *E. coli* BW3110 cells with pBW31 (the pBR plasmid which carries the hydantoinase gene) and pBW32 (the pACYC plasmid with the carbamoylase and racemase genes). Cells were induced 10 hours at 30° C.

The combination of pBW31 and 32 enables fast and complete conversion from D-L-IMH to tryptophane. The intermediate is formed up to a concentration of 0.4 mM.

Figure 6:
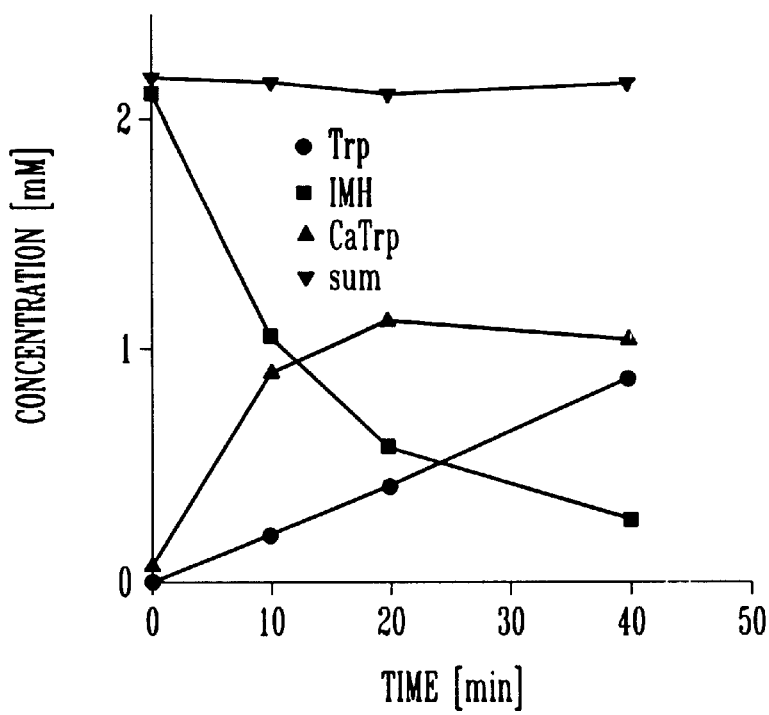
FIG. 6 shows the time course of conversions with *E. coli* BW3110 transformed with plasmids pBW34 and pBW35. Cells were induced for 10 hours at 30° C.

*E. coli* BW3110 transformed with the plasmids pBW34 (the pBR plasmid with the carbamoylase and the racemase genes) and pBW35 (the pACYC plasmid with the hydantoinase gene) was taken for this conversion. Cells were induced for 10 hours at 30° C. (FIG. 6). The combination of pBW34 and 35 shows an accumulation of the intermediate up to over 1 mM. The product formation takes place at a lower rate than seen in FIG. 5.

Figure 7:
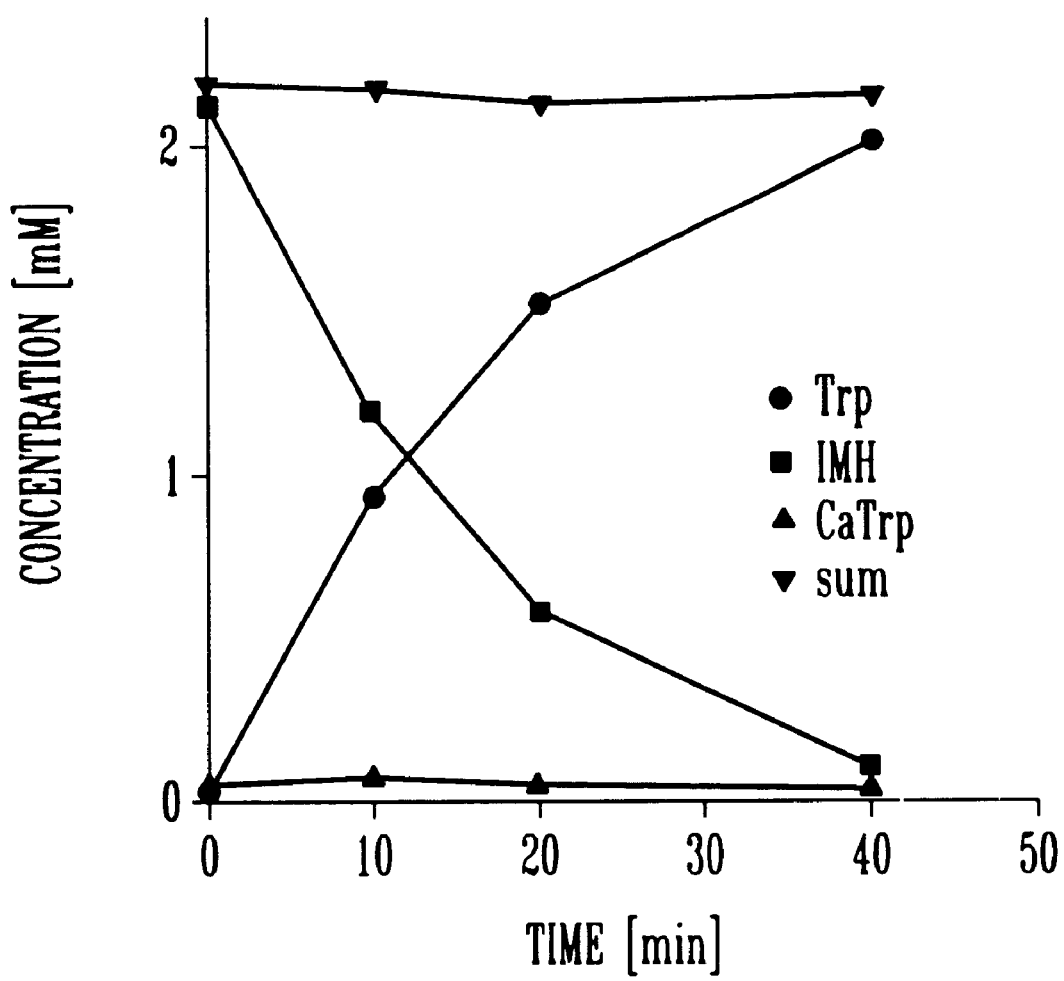
FIG. 7 shows the time course of conversions using pBW34 and pBW53.
Figure 8:
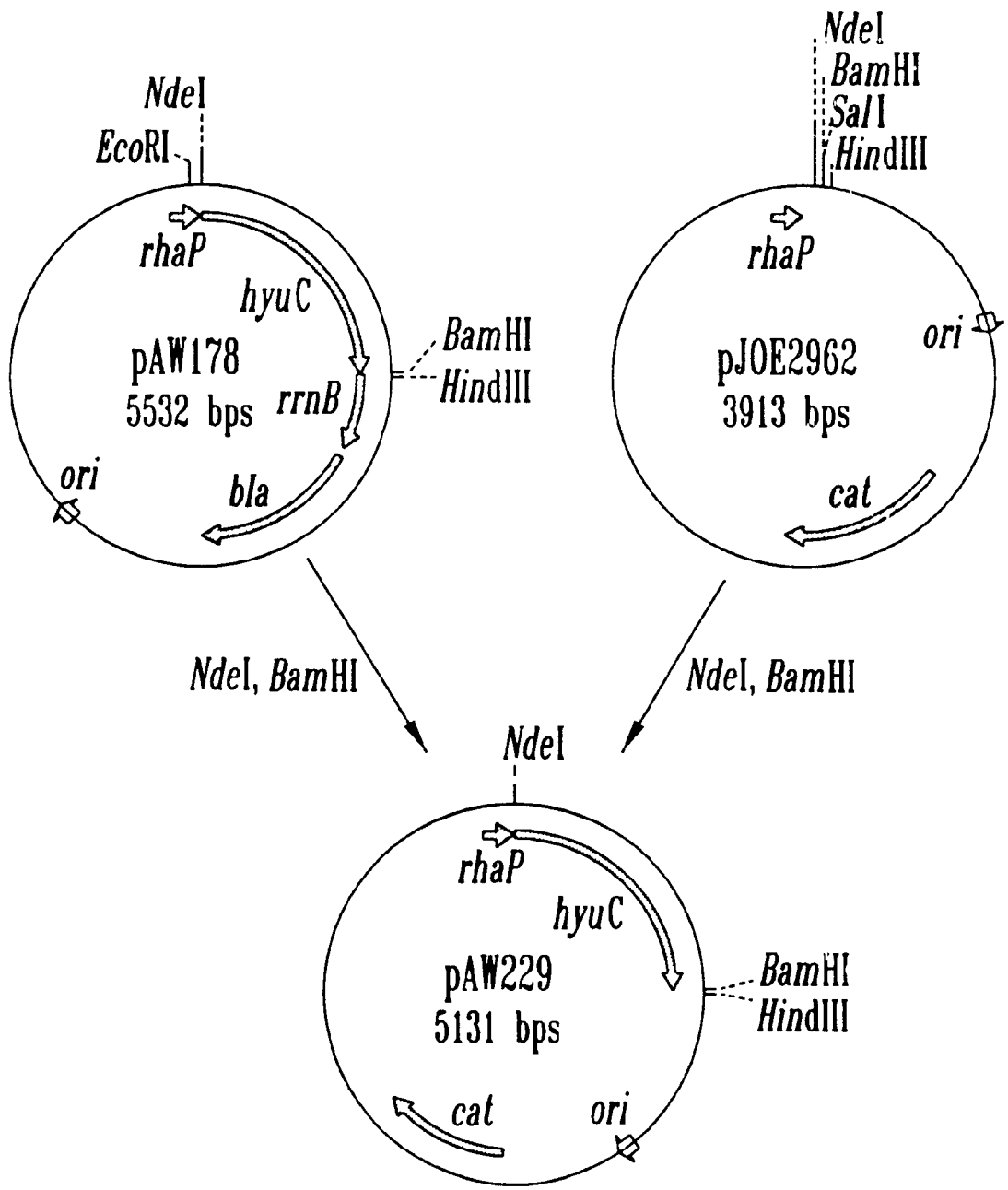
FIG. 8 shows the construction of pAW229.
Figure 9:
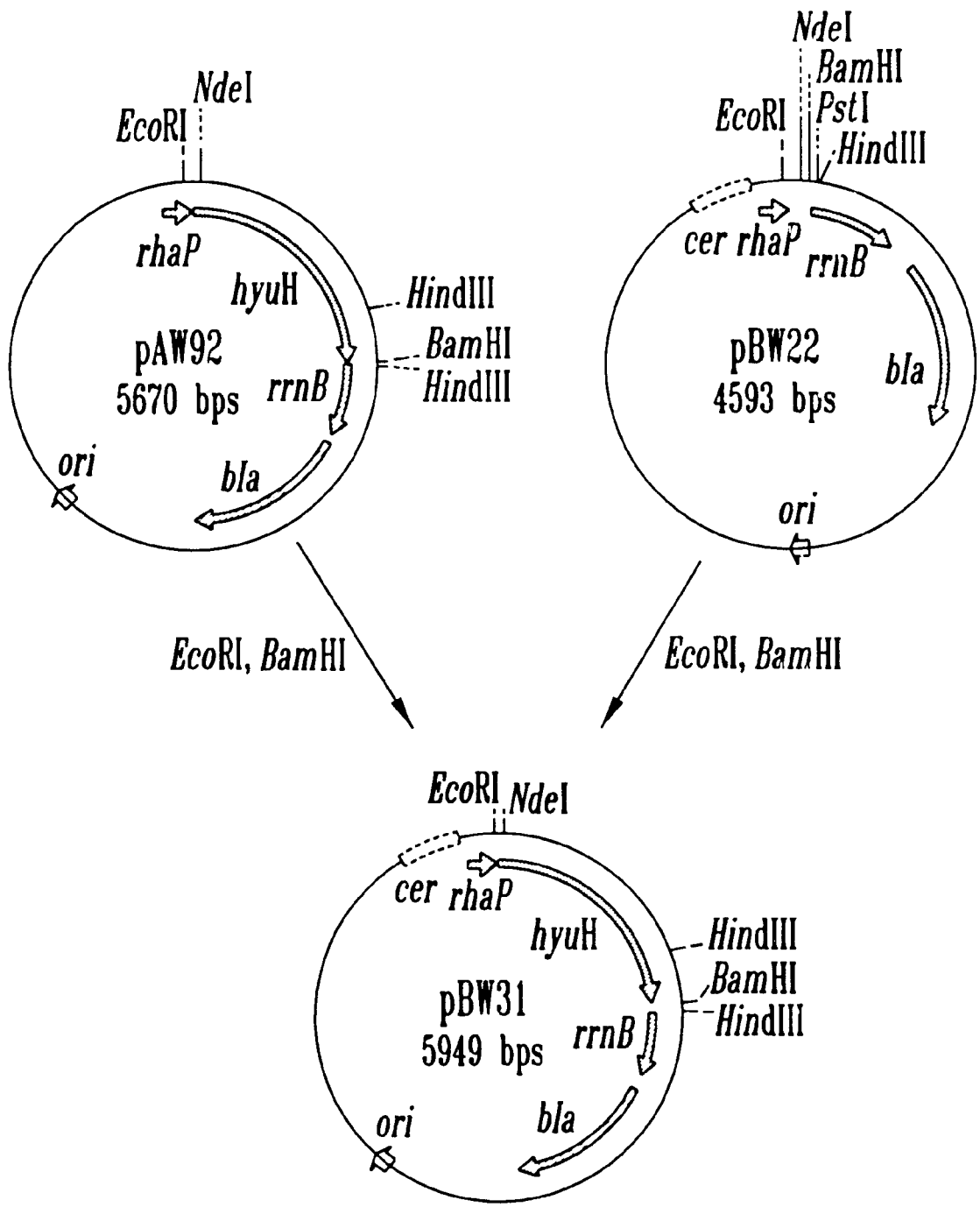
FIG. 9 shows the construction of pBW31.
Figure 10:
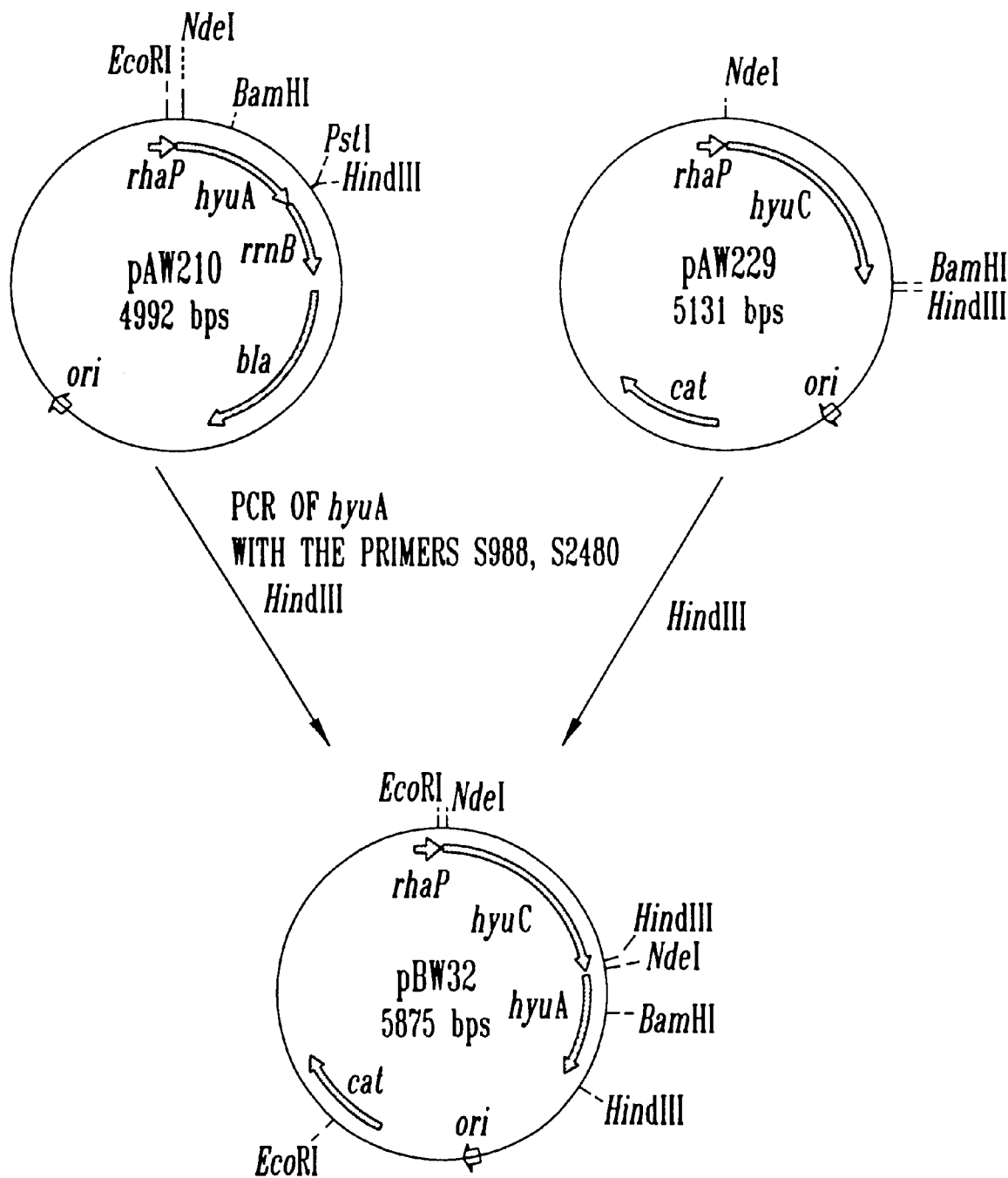
FIG. 10 shows the construction of pBW32.
Figure 11:
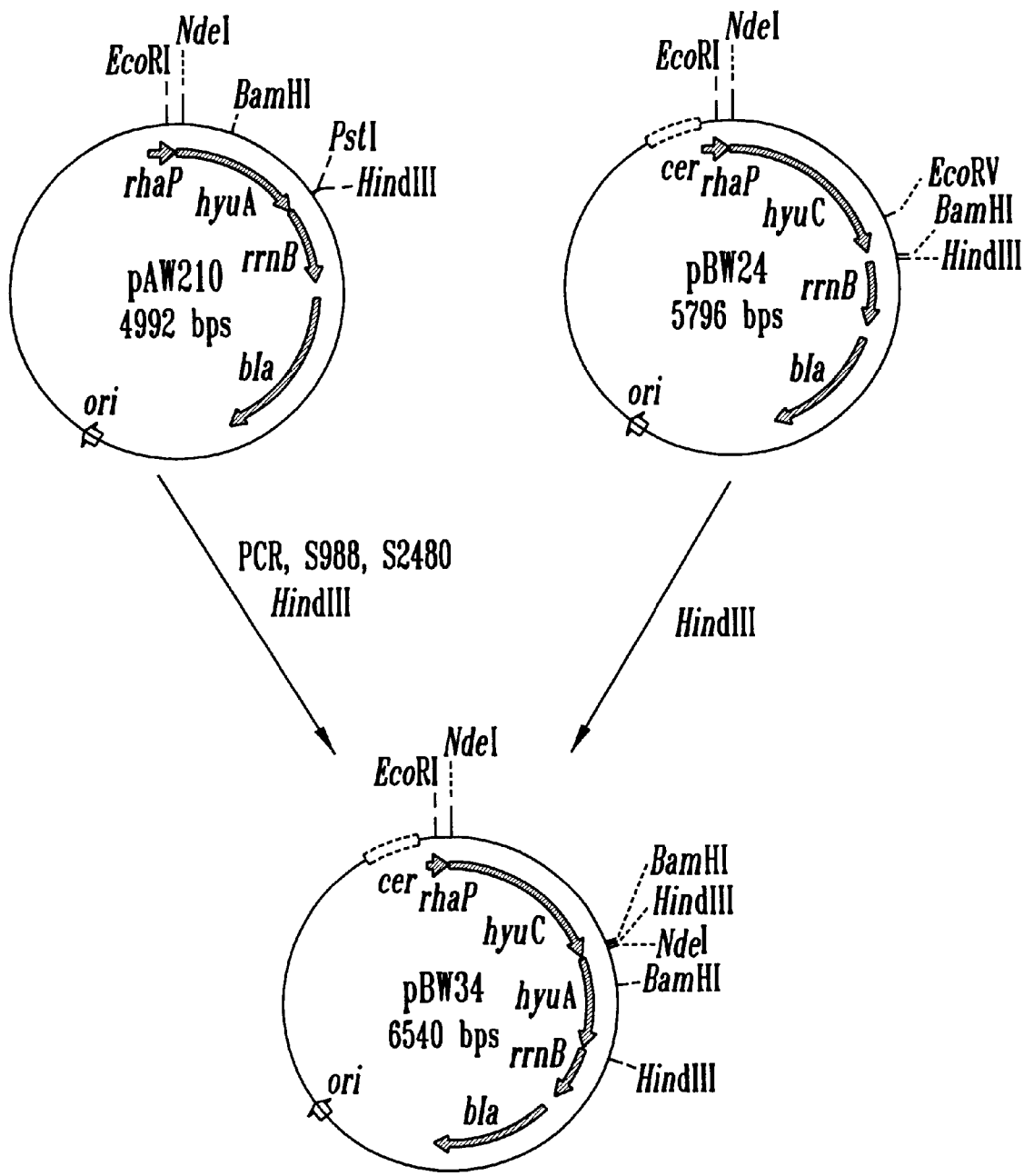
FIG. 11 shows the construction of pBW43.
Figure 12:
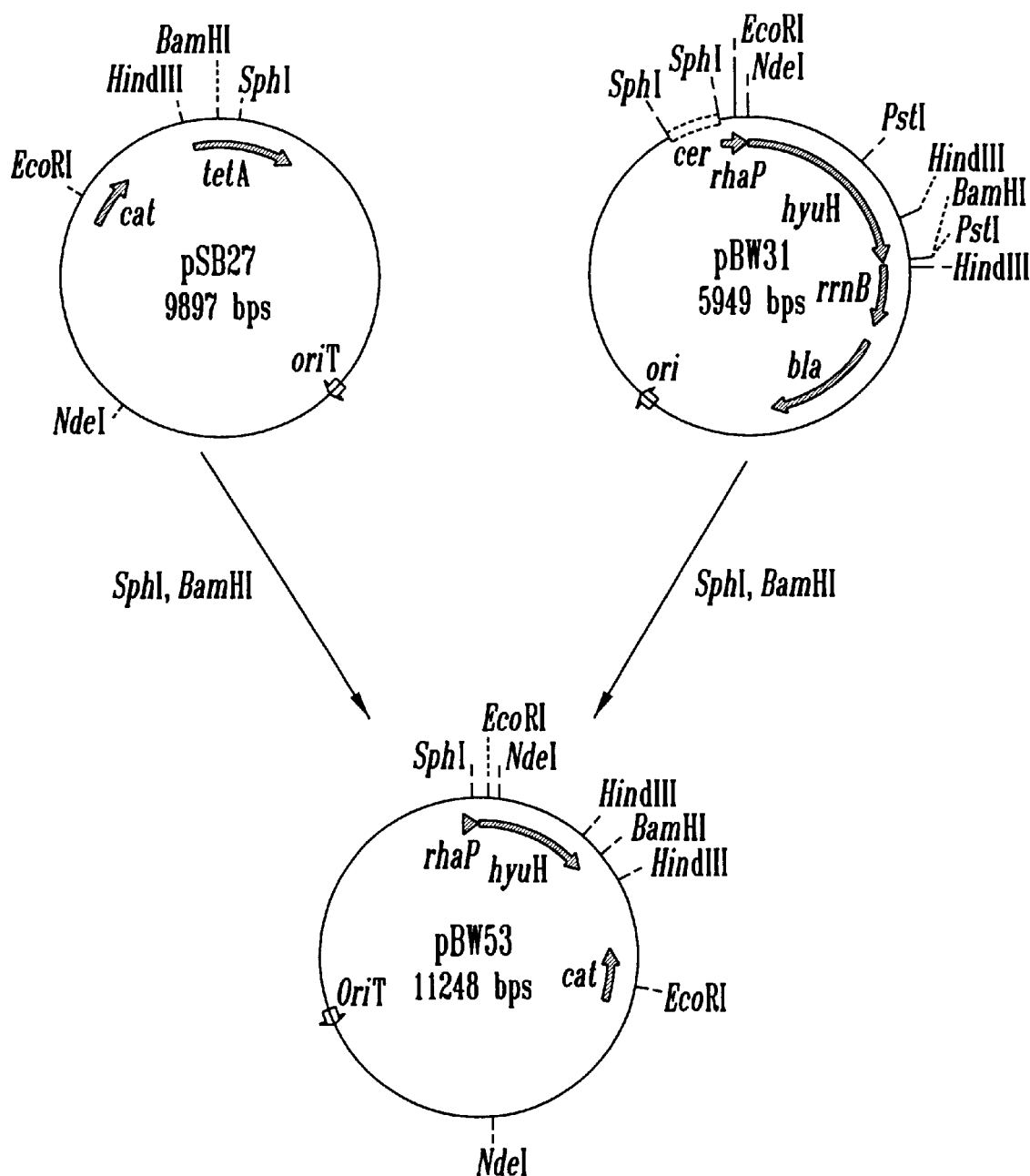
FIG. 12 shows the construction of pBW53.

Plasmid pBW34 (the pBR plasmid with the carbamoylase and the racemase genes) was combined with pBW53 (the pSC101 plasmid with the hydantoinase gene). Induction took place for 10 hours at 30° C. (FIG. 7). In this case a fast conversion of IMH to tryptophane takes place. Formation of the intermediate is strongly reduced and product formation is faster than seen in FIG. 5, so that the combination of pBW34 and pBW53 is most favourable for the process.

The present invention shows a new and superior way to combine a hydantoinase, a hydantoin racemase and a carbamoylase in a whole cell catalysator. It is this possibilty that renders instant invention to a proper method for the production of enantiomerically enriched amino acids from hydantoins due to reduction of catalyst production costs.

Enantiomerically enriched means that one antipode of a chiral compound is the major component in a mixture of both antipodes.

Amino acid denotes within the framework of this invention all compounds comprising a primary amine function connected to a carboxylic acid group via one intermediate C-atom (α-C-atom). This α-C-atom bears only one further residue. Nevertheless all natural and unnatural amino acids are deemed to be encompassed. Preferred unnatural amino acids are those mentioned in DE 19903268.8.

Genes encoding for a peptide sequence are to be understood as all genes possible with regard to the degeneration of the genetic code.

The microorganism DSM 3747 is deposited at Deutsche Sammlung für Mikroorganismen und Zellkulturen.

pBW31, pBW32, pBW34, pBW35, and pBW53 have been deposited at Deutsche Sammlung von Mikroorganismen und Zellkulturen (Mascheroder Weg 1b, D-38124 Braunschweig, Germany) on Jul. 29, 2003 and have been assigned accession numbers DSM 15809, DSM 15810, DSM 15811, DSM 15812, and DSM 15813, respectively.

EXAMPLES

Bacterial Strains, Plasmids and Growth Conditions:

E. coli JM109 (Yanisch-Perron et al. Gene (1985), 33, 103–109) was used for cloning procedures involving the hyuC (SEQ ID NO: 7), hyuH (SEQ ID NO: 9) and hyuA (SEQ ID NO: 11) genes from Arthrobacter aurescens DSM 3747 (Groβ et al., Biotech. Tech. (1987), 2, 85–90). E. coli BW3110 (Wilms et al, in preparation), a derivative of E. coli W3110 (Hill and Harnish, 1981 Proc. Natl. Acad. Sci USA 78, 7069–7072) was used for coexpression for the genes mentioned above. E. coli strains were either grown in LB liquid medium or on LB-agar plates (Luria et al., 1960, Virology 12, 348–390), both supplemented with 100 μg/ml ampicillin and/or 25 μg/ml chloramphenicol to select plasmid carrying strains. The cultures were grown at 37° C., for heterologous gene expression growth temperature was reduced to 30° C. or 25° C.

General Protocols:

All of the recombinant DNA techniques were standard methods (Sambrook et al., Molecular Cloning: A laboratory manual (1989), Cold Spring Harbour Laboratory Press, New York). PCR reactions were performed either with Pwo Polymerase or the Expand™ Long Template PCR System by following the recommendations of Roche Diagnostics.

Coexpression of hyuA, hyuC, and hyuH in E. coli:

For coexpression of the racemase gene hyuA, the carbamoylase gene hyuC, and the hydantoinase gene hyuH in E. coli, several constructions with different features were made. To obtain comparable expression levels of the genes, variations in the copy number of plasmids were used. High copy plasmids like pBR plasmids (Bolivar et al., 1977, Gene 22, 277–288) have a copy number of 40–50. PACYC184 plasmids (Chang and Cohen, 1978, J. Bacteriol., 1141–1156) have a copy number of 10–15. PSC101 plasmids (Cohen et al., 1973, Proc. Natl. Acad. Sci. USA, 70, 3240–3244) have a copy number of 5–10. A copy number of 1 is achieved by inserting the gene into the E. coli chromosome.

The plasmid features are summarized in table 1:

| plasmid name | ori | copy number | resistance | hyu - genes |
| --- | --- | --- | --- | --- |
| pAW229 | pACYC | 10–15 | cam | hyuC |
| pBW31 | pBR | 40–50 | amp | hyuH |
| pBW32 | pACYC | 10–15 | cam | hyuC + hyuA |
| pBW34 | pBR | 40–50 | amp | hyuC + hyuA |
| pBW35 | pACYC | 10–15 | cam | hyuH |
| pBW53 | pSC101 | 5–10 | cam | hyuH |

Abbreviations:
hyu: hydantoin utilizing
hyuA: racemase gene (SEQ ID NO: 11)
hyuC: carbamoylase gene (SEQ ID NO: 7)
hyuH: hydantoinase gene (SEQ ID NO: 9)
amp: ampicillin resistance (β-lactamase gene)
cam: chloramphenicol resistance (chloramphenicol acetyl transferase gene)

The hydantoinase gene hyuH was also expressed using the strain BW3110H, which carries a chromosomal insertion of the hyuH gene.

All constructs enable transcriptional regulation of gene expression by the rhaBAD promoter.

For coexpression of the carbamoylase gene hyuC and the hydantoinase gene hyuH pAW229 and pBW31 are transformed into E. coli BW3110.

For coexpression of the racemase gene hyuA, the carbamoylase gene hyuC and the hydantoinase gene hyuH, pBW31 and pBW32, pBW34 and pBW35, or pBW34 and pBW53 are suitable combinations in E. coli BW3110.

To achieve coexpression of all three Enzymes in E. coli BW3110H, pBW32 or pBW34 can be used.

Construction of the Plasmids:

pAW229 was obtained by cleaving pAW178 (Wilms et al., J. Biotechnol. (1999), 68, 101–113) with the restriction enzymes NdeI and BamHI and ligating the 1241 bp fragment containing the hyuC gene into pJOE2962 (Altenbuchner, unpublished), which was cut with the same restriction enzymes.

pBW31 was constructed by cleaving pAW92 (Wiese et al., in preparation) with the restriction enzymes EcoRI and BamHI and ligating the 1436 bp fragment containing the hyuH gene into pBW22, which was cut with the same restriction enzymes.

pBW32 was obtained by PCR amplification of the hyuA gene using the primers S988 (5'-AGGCTGAAAATCTTCTCT-3') (SEQ ID NO: 6) and S2480 (5'-AAAAAAGCTTTTAAGAAGGAGATATACATA-3') (SEQ ID NO: 1) and pAW210 (Wiese et al., in preparation) as template. Included in primer S2480 is a shine dalgarno sequence for translation initiation. The fragment was inserted into the HindIII site of pAW229.

pBW34 was created by inserting the hyuA PCR fragment described above into the HindIII site of pBW24. pBW24 was obtained by cleaving pAW178 (Wilms et al, J. Biotechnol. (1999), 68, 101–113) with NdeI and HindIII and ligating the 1261 bp long fragment containing the hyuC gene into pBW22, which was cut with the same restriction enzymes. pBW22 was constructed by PCR amplifying of the "cer"-region from the colE1 plasmid using the primers S2248 (5'-AAA GCA TGC ATG GCC CTT CGC TGG GAT-3')

(SEQ ID NO: 2) and S2249 (5'-AAA GCA TGC ATG GCT ACG AGG GCA-3') (SEQ ID NO: 3). The 268 bp fragment was cut with the restriction enzyme SphI and inserted in the vector pJOE2775 (Krebsfänger et al., 1998, Enzyme Microb. Technol. 22, 219–224) which was cut with the same restriction enzyme.

pBW35 was constructed by cleaving pBW31 with the restriction enzymes NdeI and BamHI. The 1379 bp fragment containing hyuH was inserted into pAW229, which was cut with the same restriction enzymes.

pBW53 was obtained by cleaving pBW31 with the restriction enzymes SphI and BamHI. The 1534 bp fragment containing the hyuH gene and the rhamnose promoter was inserted into pSB27 (Baumann, Dissertation, Universität Stuttgart, 1996), which was cut with the same restriction enzymes.

Construction of the Chromosomal Integrate of hyuH Into the Rhamnose Operon:

A 3.5 kb fragment from the E. coli rhamnose operon was amplified using the primers S2517 (5'-AAACAAGATCTCGCGACTGG-3') (SEQ ID NO: 4) and S2518 (5'-AAAAAGATCTTTATCAGGCCTACAACTGTTG-3') (SEQ ID NO: 5) and E. coli chromosomal DNA as template. The fragment was cut with the restriction enzyme BglII and inserted into the vector pIC20H (Marsh et al., 1984, Gene 32, 481–485), which was cut with the restriction enzymes BamHI and BglII, to get pBW39. PBW31 was cut with the restriction enzymes EcoRI and BamHI. The 1436 bp fragment containing the hyuH gene was inserted into the vector pBW39, which was also cut with the same restriction enzymes, to get pBW40. A 2.9 kb fragment was amplified using the primers S2517 and S2518 and pBW40 as a template. This fragment was cut with BglII and inserted into the vector pJOE2114 (Altenbuchner, unpublished) which was also cut with BglII to get pBW45. PBW45 was cut with BglII and SphI. The resulting 2.9 kb rhaS-rhaP-hyuH-rhaA fragment was inserted into the gene replacement vector pKO3 (Link et al, 1997, J. Bacteriol., 179, 20, 6228–6237), which was cut with BamHI. The gene replacement was carried out according to the authors' instructions. Positiv insertion events were screened using MacConckey Rhamnose plates.

Preparation of Cells and Activity Measurements:

For induction of the rhaBAD promoter strains with two plasmids were grown in $LB_{amp+cam}$, strains with one plasmid in $LB_{amp}$ or $LB_{cam}$ respectively to $OD_{600}$=0.3–0.5. Then L-rhamnose was added to a final concentration of 0.1 g $l^{-1}$ and the cultivation was continued to a final OD of approximately 5. If not indicated separately, for small scale enzyme measurements cells corresponding to $OD_{600}$ of 20 were harvested, washed in 1 ml 0.2 M Tris pH 7.0 and resuspended in 1 ml 0.2 M Tris pH 7.0, 1 mM $MnCl_2$. 10 µl toluene was added for permeabilizing the cell membranes. After 30 min of incubation at 37° C. 200 µl of this cell suspension were added to 800 µl of 2 mM D,L-Indolylmethylhydantoin (IMH) in 0.1 M Tris pH 8.5, mixed and shaked at 37° C. This cell amount corresponds to approximately 5–6 mg cell wet weight. Samples were taken regularly. The reaction was stopped by adding 14% trichloracetic acid. The time course of product and educt concentrations was determined using HPLC analysis. The HPLC-system was equipped with a RP-18 column as described previously for the determination of hydantoin derivatives and N-carbamoyl amino acids (May et al., 1998, J. Biotechnol., 26, 61 (1): 1–13). UV-absorption was measured at 280 nm and the mobile phase (0.3% (v/v) phosphoric acid (80%) and methanol (20%; v/v)) was pumped with a flow rate of 1.0 ml $min^{-1}$.

What is claimed is:

1. A microorganism which
   (A) is transformed with DNAs encoding (i) a hydantoinase, (ii) a hydantoin racemase, and (iii) a D- or L-specific carbamoylase, and
   (B) converts 5-monosubstituted hydantoins to L- or D-amino acids,
   wherein the DNAs encoding the hydantoinase, the hydantoin racemase, and the D- or L-specific carbamoylase are overexpressed in the microorganism at a rate which does not result in accumulation of intermediates in the conversion of 5-monosubstituted hydantoins to L- or D-amino acids, and
      wherein the DNAs encoding the hydantoinase, the hydantoin racemase, and the D- or L-specific carbamoylase are obtained from DSM 3747.

2. The microorganism of claim 1, which is a bacterium.

3. The microorganism of claim 1, which is an *Escherichia coli*.

4. The microorganism of claim 1, wherein the DNAs encoding the hydantoinase, the hydantoin racemase, and the D- or L-specific carbamoylase are overexpressed in a rhamnose-inducible *E. coli* promoter cassette.

5. The microorganism of claim 1, wherein the, DNA encoding the hydantoinase comprises SEQ ID NO: 8.

6. The microorganism of claim 1, wherein the DNA encoding the hydantoin racemase comprises SEQ ID NO: 10.

7. The microorganism of claim 1, wherein the DNA encoding the D- or L-specific carbamoylase comprises SEQ ID NO: 6.

8. The microorganism of claim 1, wherein
   the DNA encoding the hydantoinase comprises SEQ ID NO: 8,
   the DNA encoding the hydantoin racemase comprises SEQ ID NO: 10, and
   the DNA encoding the D- or L-specific carbamoylase comprises SEQ ID NO: 6.

9. The microorganism of claim 1, wherein the DNA encoding the hydantoinase encodes an amino acid sequence comprising SEQ ID NO: 9.

10. The microorganism of claim 1, wherein the DNA encoding the hydantoin racemase encodes an amino acid sequence comprising SEQ ID NO: 11.

11. The microorganism of claim 1, wherein the DNA encoding the D- or L-specific carbamoylase encodes an amino acid sequence comprising SEQ ID NO: 7.

12. The microorganism of claim 1, wherein
   the DNA encoding the hydantoinase encodes an amino acid sequence comprising SEQ ID NO: 9,
   the DNA encoding the hydantoin racemase encodes an amino acid sequence comprising SEQ ID NO: 11, and
   the DNA encoding the D- or L-specific carbamoylase encodes an amino acid sequence comprising SEQ ID NO: 7.

13. The microorganism of claim 1, which is transformed with at least one plasmid containing the DNAs encoding the hydantoinase, the hydantoin racemase, and the D- or L-specific carbamoylase.

14. A process for producing the microorganism of claim 1, comprising:
   transforming a microorganism with one or more plasmids containing the DNAs encoding the hydantoinase, the hydantoin racemase, and the D- or L-specific carbamoylase.

15. The process of claim 14, wherein the plasmids are selected from the group consisting of pBW31, pBW32, pBW34, pBW35, and pBW53.

16. The process of claim 14, wherein the plasmids are pBW31 and pBW32, pBW34 and pBW35, pBW34 and pBW53, or pBW32 and pBW34.

17. The process of claim 14, wherein the plasmids are derived from pSC101, pACYC184, or pBR322.

18. The process of claim 14, wherein the microorganism is an *E. coli* having a chromosomally inserted hydantoinase gene.

19. The process of claim 14, in which a rhamnose inducible *E. coli* promoter cassette is used.

20. A process for the production of enantiomerically enriched amino acids, comprising culturing the microorganism of claim 1 in a culture medium.

21. The process of claim 20, which is performed in a enzyme-membrane reactor.

22. A microorganism which
(A) is transformed with DNAs encoding (i) a hydantoinase, (ii) a hydantoin racemase, and (iii) a D- or L-specific carbamoylase, and
(B) converts 5-monosubstituted hydantoins to L- or D-amino acids,
wherein the DNAs encoding the hydantoinase, the hydantoin racemase, and the D- or L-specific carbamoylase are overexpressed in a microorganism at a rate which does not result in accumulation of intermediates in the conversion of 5-monosubstituted hydantoins to L- or D-amino acids, and wherein
the DNA encoding the hydantoinase encodes an amino acid sequence comprising SEQ ID NO: 9,
the DNA encoding the hydantoin racemase encodes an amino acid sequence comprising SEQ ID NO: 11,
the DNA encoding the D- or L-specific carbamoylase encodes an amino acid sequence comprising SEQ ID NO: 7.

23. The microorganism of claim 22, which is a bacterium.

24. The microorganism of claim 22, which is an *Escherichia coli*.

25. The microorganism of claim 22, wherein the DNAs encoding the hydantoinase, the hydantoin racemase, and the D- or L-specific carbamoylase are obtained from DSM 3747.

26. The microorganism of claim 22, wherein the DNAs encoding the hydantoinase, the hydantoin racemase, and the D- or L-specific carbamoylase are overexpressed in a rhamnose-inducible *E. coli* promoter cassette.

27. The microorganism of claim 22, wherein the DNA encoding the hydantoinase comprises SEQ ID NO: 8.

28. The microorganism of claim 22, wherein the DNA encoding the hydantoin racemase comprises SEQ ID NO: 10.

29. The microorganism of claim 22, wherein the DNA encoding the D- or L-specific carbamoylase comprises SEQ ID NO: 6.

30. The microorganism of claim 22, which is transformed with at least one plasmid containing the DNAs encoding the hydantoinase, the hydantoin racemase, and the D- or L-specific carbamoylase.

31. A process for producing the microorganism of claim 22, comprising:
transforming a microorganism with one or more plasmids containing the DNAs encoding the hydantoinase, the hydantoin racemase, and the D- or L-specific carbamoylase.

32. The process of claim 31, wherein the plasmids are selected from the group consisting of pBW31, pBW32, pBW34, pBW35, and pBW53.

33. The process of claim 31, wherein the plasmids are pBW31 and pBW32, pBW34 and pBW35, pBW34 and pBW53, or pBW32 and pBW34.

34. The process of claim 31, wherein the plasmids are derived from pSC101, pACYC184, or pBR322.

35. The process of claim 31, wherein the microorganism is an *E. coli* having a chromosomally inserted hydantoinase gene.

36. The process of claim 31, in which a rhamnose inducible *E. coli* promoter cassette is used.

37. A process for the production of enantiomerically enriched amino acids, comprising culturing the microorganism of claim 22 in a culture medium.

38. The process of claim 37, which is performed in a enzyme-membrane reactor.

39. A microorganism which
(A) is transformed with DNAs encoding (i) a hydantoinase, (ii) a hydantoin racemase, and (iii) a D- or L-specific carbamoylase, and
(B) converts 5-monosubstituted hydantoins to L- or D-amino acids,
wherein the DNAs encoding the hydantoinase, the hydantoin racemase, and the D- or L-specific carbamoylase are overexpressed in a microorganism at a rate which does not result in accumulation of intermediates in the conversion of 5-monosubstituted hydantoins to L- or D-amino acids, and wherein
the DNA encoding the hydantoinase encodes an amino acid sequence consisting of SEQ ID NO: 9,
the DNA encoding the hydantoin racemase encodes an amino acid sequence consisting of SEQ ID NO: 11,
the DNA encoding the D- or L-specific carbamoylase encodes an amino acid sequence consisting of SEQ ID NO: 7.

40. The microorganism of claim 39, which is a bacterium.

41. The microorganism of claim 39, which is an *Escherichia coli*.

42. The microorganism of claim 39, wherein the DNAs encoding the hydantoinase, the hydantoin racemase, and the D- or L-specific carbamoylase are obtained from DSM 3747.

43. The microorganism of claim 39, wherein the DNAs encoding the hydantoinase, the hydantoin racemase, and the D- or L-specific carbamoylase are overexpressed in a rhamnose-inducible *E. coli* promoter cassette.

44. The microorganism of claim 39, wherein the DNA encoding the hydantoinase consists of SEQ ID NO: 8.

45. The microorganism of claim 39, wherein the DNA encoding the hydantoin racemase consists of SEQ ID NO: 10.

46. The microorganism of claim 39, wherein the DNA encoding the D- or L-specific carbamoylase consists of SEQ ID NO: 6.

47. The microorganism of claim 39, wherein
the DNA encoding the hydantoinase comprises SEQ ID NO: 8,
the DNA encoding the hydantoin racemase comprises SEQ ID NO: 10, and
the DNA encoding the D- or L-specific carbamoylase comprises SEQ ID NO: 6.

48. The microorganism of claim 39, which is transformed with at least one plasmid containing the DNAs encoding the hydantoinase, the hydantoin racemase, and the D- or L-specific carbamoylase.

49. A process for producing the microorganism of claim 39, comprising:
transforming a microorganism with one or more plasmids containing the DNAs encoding the hydantoinase, the hydantoin racemase, and the D- or L-specific carbamoylase.

50. The process of claim 49, wherein the plasmids are selected from the group consisting of pBW31, pBW32, pBW34, pBW35, and pBW53.

51. The process of claim 49, wherein the plasmids are pBW31 and pBW32, pBW34 and pBW35, pBW34 and pBW53, or pBW32 and pBW34.

52. The process of claim 49, wherein the plasmids are derived from pSC101, pACYC184, or pBR322.

53. The process of claim 49, wherein the microorganism is an *E. coli* having a chromosomally inserted hydantoinase gene.

54. The process of claim 49, in which a rhamnose inducible *E. coli* promoter cassette is used.

55. A process for the production of enantiomerically enriched amino acids, comprising culturing the microorganism of claim 39 in a culture medium.

56. The process of claim 55, which is performed in a enzyme-membrane reactor.

* * * * *

UNITED STATES PATENT AND TRADEMARK OFFICE
CERTIFICATE OF CORRECTION

PATENT NO. : 6,713,288 B1
DATED : March 30, 2004
INVENTOR(S) : Josef Altenbuchner et al.

Figure 13:
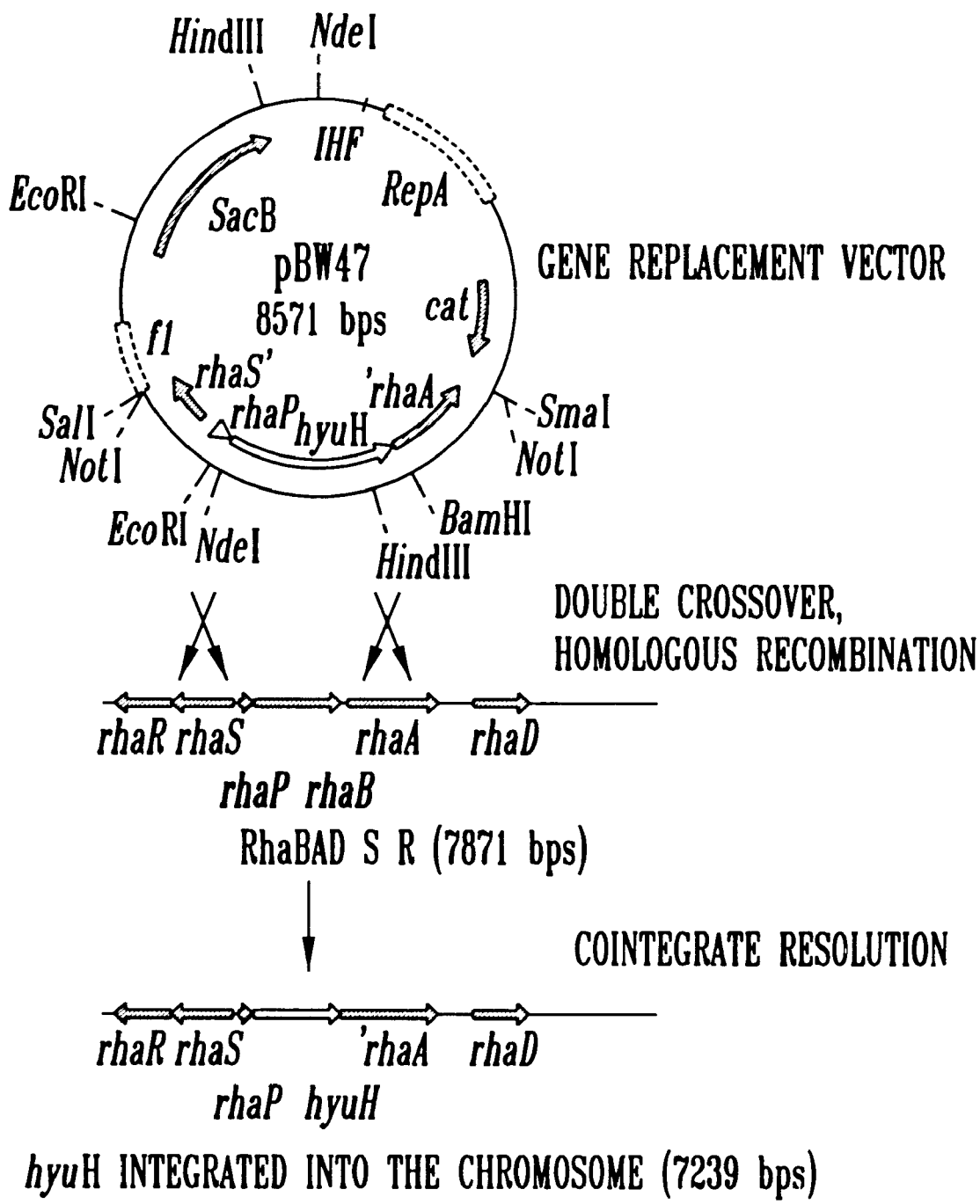

It is certified that error appears in the above-identified patent and that said Letters Patent is hereby corrected as shown below:

Column 4,
Line 24, add the following
-- FIG. 13 shows the chromosomal insertion of hyuH. --.

Signed and Sealed this

First Day of November, 2005

JON W. DUDAS
*Director of the United States Patent and Trademark Office*